United States Patent

Savisalo et al.

[11] Patent Number: 4,933,292
[45] Date of Patent: Jun. 12, 1990

[54] METHOD FOR CONTROLLING AND MEASURING CELLULOSE DIGESTION

[75] Inventors: Hannu Savisalo; Timo Kerola, both of Mikkeli, Finland

[73] Assignee: Savcor-Consulting Oy, Finland

[21] Appl. No.: 94,319

[22] Filed: Sep. 4, 1987

[30] Foreign Application Priority Data

Sep. 8, 1986 [FI] Finland ................... 863615

[51] Int. Cl.$^5$ ................ C12P 7/28; D21C 7/12
[52] U.S. Cl. .................... 436/150; 162/49; 162/50
[58] Field of Search .............. 436/150; 204/411, 412, 204/403; 162/49, 50

[56] References Cited

U.S. PATENT DOCUMENTS

| | | | |
|---|---|---|---|
| 3,886,034 | 5/1975 | Noreus | 162/49 |
| 3,888,726 | 6/1975 | Hultman | 162/49 |
| 3,941,649 | 3/1976 | Wallin | 162/49 |
| 4,536,253 | 8/1985 | Bertelsen | 436/150 |
| 4,624,742 | 11/1986 | Klein et al. | 162/49 |

Primary Examiner—Barry S. Richman
Assistant Examiner—T. J. Wallen
Attorney, Agent, or Firm—Steinberg & Raskin

[57] ABSTRACT

A procedure for controlling cellulose digestion by measuring activity of chemicals essentially influencing the cellulose digestion and which are present in a cellulose digester. Feeding of chemicals to be added into the cellulose digester is controlled on the basis of the measurement results. The measurement is carried out by placing, in the cellulose digester, one or several measuring electrodes and reference electrodes, and a current-supplying counterelectrode. Current is supplied to the thus-established circuit from a current source, in a manner such that the voltage across the measuring electrode and the reference electrode, in other words the electrochemical potential of the measuring electrode, is substantially constant. The current intensity corresponding to such potential is directly proportional to activity of the chemicals in the cellulose digester. A method for measuring the cellulose digestive activity is also provided in accordance with the present invention.

13 Claims, 2 Drawing Sheets

METHOD FOR CONTROLLING AN MEASURING CELLULOSE DIGESTION

BACKGROUND OF THE INVENTION

The present invention concerns a procedure for controlling cellulose digestion by measuring the activity of chemicals which essentially affect the cellulose digestion and which are present in a cellulose digester, with supplying of ingredients or chemicals to be added into the cellulose digester being controlled on the basis of the measurement results. The present invention is also directed to a method for measuring the cellulose digestive activity itself within the cellulose digester.

Information on various processing variables is required in the control of cellulose digestion. The progress of the digesting process is also followed with the aid of dissolving lignin, in addition to control of the incoming and outgoing pulp flow. Determining the lignin content of the pulp itself, would best reflect the progress of digestion. However, such determination is too time-consuming. It is moreover exceedingly difficult to obtain a representative sample of the pulp during the digestion. For these reasons, the monitoring of digestion has been restricted to analyzing the chemicals concentrations of the digesting solution. The variable on which attention is most commonly focussed is the active or effective alkali. The most common analytic method for determining the effective alkali is based on titration. Perhaps best known among computer-controlled analyzers of effective alkali in continuous-action digestion, is the apparatus in which titration is carried out with carbon dioxide. Titration is effected under pressure by measuring the reaction temperature and determining the end-point of titration from a titration graph with the aid of a computer. Apparatus based on calorimetric titration has also been developed for analysis of effective alkali.

A drawback encumbering these methods is that in the sampling, process samples cannot be taken at arbitrary points in the cellulose digester, so that the sample is not sufficiently representative. Moreover, analysis is based on content, not on activity. This detracts from the reliability of results. The apparatus designs are expensive and complex, this meaning high chances of error. Maintenance also involves considerable expense.

Conductivity measurement has been increasingly employed towards measuring effective alkali, this method being simple and inexpensive. However, several factors exert influence on conductivity, such as temperature, sodium carbonate, and sodium sulfide, so that changes in the same have to be taken into account.

However, the selectivity of conductivity measurement is not good enough, because the measuring technique fails to react sufficiently swiftly to ions. Problems and errors in measurement are furthermore caused by electrode contamination. Cleaning and recalibration and measurement which are necessary thereafter, increase the operating costs.

The use of an ion-selective electrode is based on the activity of the ion, which can be thought of as a kind of effective concentration. The potential which the electrode yields is a function of the logarithm of activity. Best known among ion-selective electrodes is the pH pick-up, its output value being a function of the logarithm of the hydrogen ion activity.

The advantages of a measuring method based on ion selectivity include the placeability of pick-ups in the process flow, whereby there is no need to provide for sampling, which is often quite cumbersome. With ion-selective electrodes used in conjunction with the sulfate process, slightly better selectivity of information is achieved as compared with other analytic methods which are practiced, although this selectivity is still not good enough. For this application, sodium and sulfide electrodes are commercially available, in addition to the pH electrode.

All the methods outlined in the foregoing have either the drawback that they require inconvenient sampling, or the drawback that the results of analysis are not selective enough.

SUMMARY OF THE INVENTION

Accordingly, it is an object of the present invention to provide a procedure in which the drawbacks associated with the procedures of the prior art are avoided.

It is also an object of the present invention to improve sampling technique in the method and control of cellulose digestion.

It is an additional object to improve selectivity of measurement in the measuring and analysis of cellulose digestive activity.

It is a further object of the present invention to improve accuracy in determining cellulose digestive activity.

It is another object of the present invention to improve the ease of measuring cellulose digestive activity.

These and other objects are attained by the present invention which is directed to a method for controlling cellulose digestion by measuring activity of chemicals which influence cellulose digestion and which are present in a cellulose digester, so that the feeding of ingredients to the cellulose digester can be controlled on the basis of the measuring results. At least one measuring electrode, at least one reference electrode, and a current-supplying counterelectrode are placed in the cellulose digester to establish a circuit, with current being supplied to the thus-established circuit from a current source in a manner such that a predetermined voltage between the measuring electrode and the reference electrode, which represents electrochemical potential of the measuring electrode, is obtained. The current intensity corresponding to this electrochemical potential is directly proportional to the activity of the chemicals within the cellulose digester. The predetermined voltage is preferably substantially constant.

The present invention is also directed to a method for measuring cellulose digestive activity, which comprises placing at least one measuring electrode, at least one reference electrode, and a current-supplying counterelectrode in a cellulose digester to establish a circuit. Current is supplied to the thus-established circuit from a current source to obtain a predetermined voltage between the measuring electrode and the reference electrode, with such current intensity, being an indicator of the cellulose digestive activity, then being measured.

Therefore, in order to accomplish these objects and those which will become apparent below, the present invention is principally characterized by measurement being performed by placing, in the cellulose digester, one or several measuring electrodes and reference electrodes, and a current-supplying counterelectrode, with electric current being supplied from a current source into the circuit thus established in a manner such that the voltage across the measuring electrode and the reference electrode, in other words the electrochemical potential of the measuring electrode, is substantially constant during the measurement, in which case the current intensity corresponding to the respective potential is directly proportional to the activity of the chemicals.

The present invention makes use of the relationship between the current density of a dissolving electrode and the chemicals concentrations. In the measurement, a metallic surface is used which, with a suitable electric current, has been transformed into active state so that it will best react to changes in the desired ion concentration. The alkali content and the sulphidity of the digesting liquor and their changes are most clearly and rapidly discernible in the current densities of an appropriate dissolving metal.

The procedure of the present invention provides a further advantage over the state of the art, in that one may, without apprehension, install a plurality of measuring pick-ups in various parts of the digesting vessel, whereby the sample will be representative. The measuring electrodes consist of metal and are therefore mechanically durable. Since a dissolving electrode is employed for measurement, contamination of the pick-up causes no problem. By this procedure, data are rapidly and accurately obtained concerning the chemicals concentration in cellulose digesting, in a manner enabling the same to be used to control the chemical inputs.

In the procedure of the present invention, a measuring pick-up has been installed in the cellulose digester with the aid of wall-traversing inlets, this pick-up comprising a metallic measuring electrode, a current-supplying counterelectrode, and a reference electrode measuring electrochemical potential. The test body and counterelectrode of the measuring pick-up form a circuit which is supplied with electric current from a current source in a manner such that the preset voltage across the reference electrode and the test body is held constant. With this arrangement, the current intensity in the circuit is dependent upon the chemicals concentration in the digesting liquor.

The quantity of effective alkali is directly proportional to the current intensity in the measuring circuit. The current passes between the measuring electrode and the counterelectrode when, in the potentiostatic circuit, the differential voltage between the measuring electrode and the counterelectrode has been adjusted to have a suitable magnitude.

In determination both of alkalinity and of sulphidity, the suitable voltage is in the range from about $-500$ to about $-1500$ mV with reference to a calomel electrode. The measuring electrode may consist of carbon steel, iron, copper, zinc, cadmium of monel metal. The reference electrode may be any electrode which is compatible with the system.

BRIEF DESCRIPTION OF THE DRAWINGS

The present invention will now be described in detail with reference to a preferred embodiment thereof illustrated in the drawings, to which the present invention is not intended to be exclusively confined. In the drawings.

DESCRIPTION OF THE PREFERRED EMBODIMENTS

Figure 1:
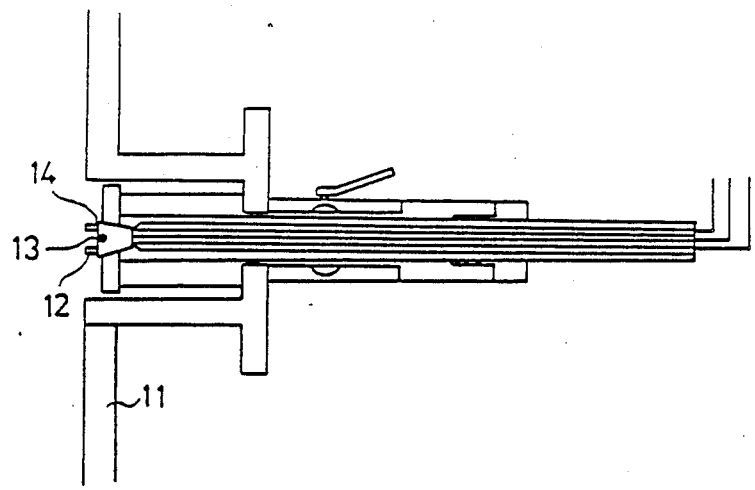
FIG. 1 is a schematic elevational view of a pick-up design applied in a cellulose digester for implementing the procedure of the present invention.

One manner of introducing a pick-up into a cellulose digester is depicted in FIG. 1. Clearly, the pick-up may be equally arranged in another manner. Moreover, the circuit itself may be disposed in another manner, without departing from the inventive concepts of the present invention herein.

Figure 4:
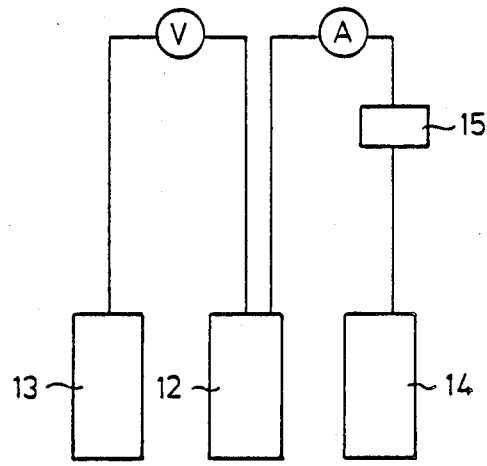
FIG. 4 is a schematic diagram of a circuit used in the procedure of the present invention.

In the embodiment of FIGS. 1 and 4, the wall of the cellulose digester has been indicated by reference numeral 11, the measuring electrode by reference numeral 12, the reference electrode by reference numeral 13, and the counterelectrode by reference numeral 14. In the circuit diagram of FIG. 4, the current source has been denoted by reference numeral 15.

Figure 2:
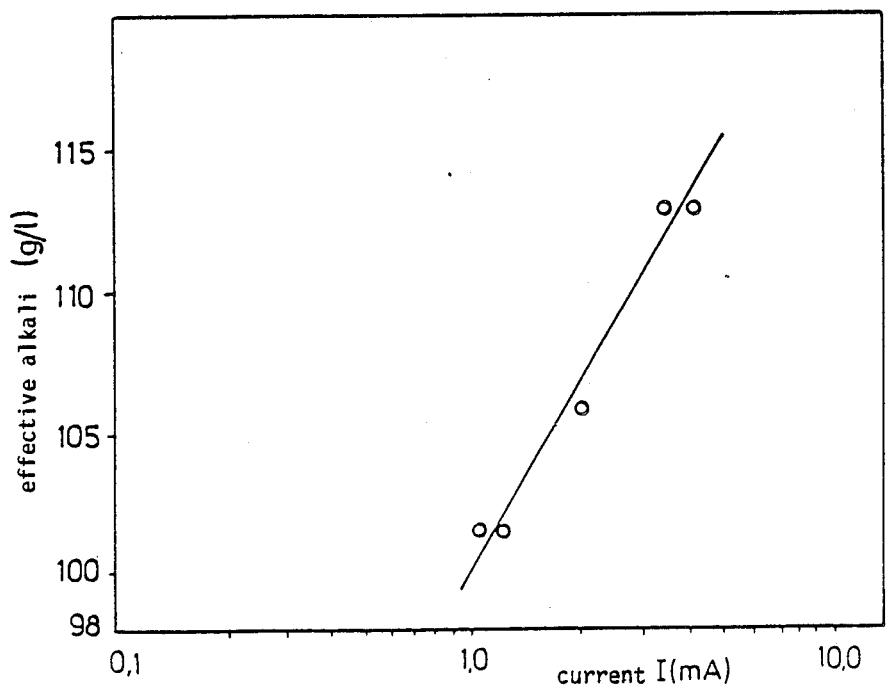
FIG. 2 is a graphic illustration of results of measurement obtained when using the procedure of the present invention.

Some results of measurement which have been obtained using the procedure of the present invention are presented in FIG. 2. In this figure, the y axis represents the quantity of effective alkali in units of g/l, while the x axis represents the current I flowing in the measuring circuit, in units of mA. The current intensity I has been found from the current flowing between the measuring electrode 12 and the counterelectrode 14 when the differential voltage between the measuring electrode 12 and the reference electrode 13 in the potentiostatic circuit has been adjusted to a suitable value.

Figure 3:
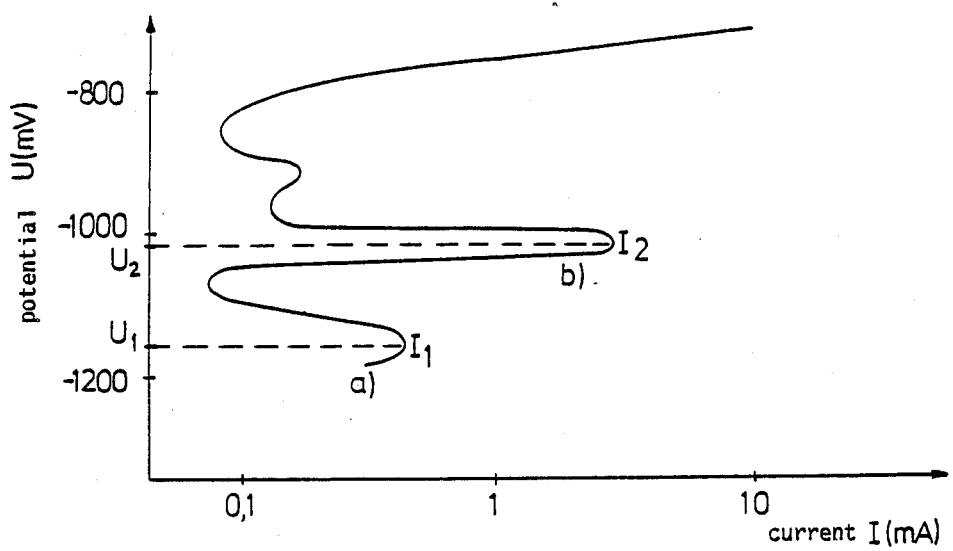
FIG. 3 is a graphic illustration of the relationship of current intensity:potential of two different ions.

The procedure of the present invention is highly selective with respect to different ions. In FIG. 3, a schematic diagram is presented illustrating the current intensity/potential relationship for two different ions, (a) and (b). The most favorable situation is obtained when $U_1$ corresponds to the current intensity $I_1$ and $U_2$ corresponds to the current intensity $I_2$.

The preceding description of the present invention is merely exemplary, and is not intended to limit the scope thereof in any way.

I claim:

1. Method for controlling cellulose digestion by measuring activity of chemicals which influence cellulose digestion and which are present in a cellulose digester, comprising placing in digesting liquor within the cellulose digester, at least one measuring electrode, at least one reference electrode, and a current-supplying counterelectrode to establish a circuit;

while digestion is being carried out in said digester, supplying current to the thus-established circuit from a current source in a manner such that a predetermined voltage between the measuring electrode and the reference electrode, which represents maintaining the voltage between the measuring electrode and the reference electrode substantially constant and measuring current flowing between the measuring electrode and counterelectrode in said digester while said voltage is substantially constant, which is current intensity corresponding to said electrochemical potential and is directly proportional to the cellulose digestive activity of said chemicals whereby the cellulose digestive activity is continuously determined directly in the cellulose digester, and feeding ingredients into the digesting liquor within the cellulose digester based on said measuring results of current intensity, so that the feeding of ingredients into the cellulose digester can be controlled on the basis of the measuring results.

2. The method of claim 1, additionally comprising measuring change of current intensity in the cellulose digester as a function of change in chemicals concentration within the digester.

3. The method of claim 1, wherein the predetermined voltage is from about −500 to about −1500 mV.

4. The method of claim 1, additionally comprising placing a plurality of the measuring electrodes in various parts of the digester,
whereby the cellulose digestive activity in the liquor is representatively determined at various points along the digester.

5. The method of claim 1, additionally comprising placing several reference electrodes in various parts of the cellulose digester.

6. The method of claim 1, wherein the measuring electrode consists of metal and is therefore mechanically durable.

7. Method for measuring cellulose digestion activity within a cellulose digester, comprising
placing in digesting liquor within the cellulose digester, at least one measuring electrode, at least one reference electrode, and a current-supplying counterelectrode to establish a circuit,
while digestion is being carried out in said digester, supplying current to the thus-established circuit to obtain a predetermined voltage between the measuring electrode and the reference electrode, and maintaining said voltage between the measuring electrode and the reference electrode substantially constant, and measuring current intensity required to obtain said predetermined voltage while said voltage is substantially constant, said current intensity being a measure of current flowing between said measuring electrode and counterelectrode and being directly proportional to the cellulose digestive activity,
whereby the cellulose digestive activity is continuously determined directly in the cellulose digester.

8. The method of claim 7, additionally comprising feeding ingredients into the cellulose digester based on the measured current intensity.

9. The method of claim 7 wherein the quality of alkali within the cellulose digester is determined by measuring the current intensity, said quality of alkali being directly proportioned to the current intensity.

10. The method of claim 7, wherein the predetermined voltage is from about −500 to about −1500 mV with respect to a calomel electrode.

11. The method of claim 7, additionally comprising placing a plurality of the measuring electrodes in various parts of the digester,
whereby the cellulose digestive activity in the liquor is representatively determined at various points along the digester.

12. The method of claim 11, additionally comprising placing several reference electrodes in various parts of the cellulose digester.

13. The method of claim 7, wherein the measuring electrode consists of metal and is therefore mechanically durable.

* * * * *